United States Patent [19]

Harrison, Jr. et al.

[11] 4,256,876

[45] Mar. 17, 1981

[54] PROCESS FOR PRECIPITATING AMINOGLYCOSIDES

[75] Inventors: Roger G. Harrison, Jr., Kalamazoo; Thomas H. Prichard, Portage, both of Mich.

[73] Assignee: The Upjohn Company, Kalamazoo, Mich.

[21] Appl. No.: 118,408

[22] Filed: Feb. 4, 1980

[51] Int. Cl.³ .............................................. C07H 1/06
[52] U.S. Cl. ........................................ 536/12; 536/9; 536/10; 536/17 A; 536/17 R
[58] Field of Search ................... 536/10, 12, 17 R, 9, 536/17 A

[56] References Cited

U.S. PATENT DOCUMENTS 2,799,620  7/1957  Waksman et al. ...................... 536/12
3,091,572  5/1963  Luedemann et al. .................. 536/17
3,651,042  3/1972  Marquez et al. ....................... 536/17

OTHER PUBLICATIONS

Rosselet et al., "Antimicrob. Agents & Chemotherapy", pp. 14–16, 1963.
Wagman et al., "The Jour. of Antibiotics", vol. 23, pp. 555–558, 1970.
Korzeniowski et al., "Principles and Practice of Infectious Disease", G. L. Mandell et al. (Eds.), Wiley & Sons, N. Y. 1979, pp. 249–251 & 268.

*Primary Examiner*—Johnnie R. Brown
*Attorney, Agent, or Firm*—Roman Saliwanchik

[57] ABSTRACT

A highly efficient process for the precipitation of an amorphous (non-crystalline) aminoglycoside antibiotic salt during the purification process. Illustratively, there are disclosed processes for precipitating gentamicin, neomycin, and sisomicin salts.

9 Claims, No Drawings

PROCESS FOR PRECIPITATING AMINOGLYCOSIDES

DESCRIPTION

Background of the Invention

Aminoglycoside antibiotics are a well-known class of useful antibiotics. Notable among these are gentamicin, neomycin, sisomicin, and the like. The gentamicin fermentation and recovery are disclosed in U.S. Pat. No. 3,091,572. The neomycin fermentation and recovery are disclosed in U.S. Pat. No. 2,799,620. Sisomicin preparation is disclosed in *J. Antibiotics*, Vol. 23, 555 (1970).

Aminoglycoside antibiotics are generally converted to a desired salt form during recovery and purification procedures. For example, gentamicin, advantageously, is converted to the sulfate. A prior art process for preparing gentamicin sulfate is disclosed in U.S. 3,091,572. A key step in such a process is the precipitation of gentamicin sulfate from an aqueous solution containing the same. The efficiency of this precipitation step, which is directly related to a certain desired particle size, has a large bearing on the efficiency of the purification process. In U.S. Pat. No. 3,091,572, an aqueous solution of gentamicin sulfate at pH 4.5 is added to methanol. The disclosed patent process does not recognize any critical features during this key precipitation step. Thus, the patent disclosure teaches that a 40 g./liter aqueous solids concentration of gentamicin sulfate and 10 volumes of methanol per volume of aqueous are used in the precipitation step. Similar conditions were used for precipitating gentamicin sulfate in a subsequent publication. See Rosselet, J. P., et al., "Isolation, Purification, and Characterization of Gentamicin," *Antimicrob. Agents Chemotther.*, 14–16 (1963). Also, the process disclosed in U.S. Pat. No. 3,651,042 utilizes the above conditions and uses an aqueous solids concentration of 250 mg./ml. of gentamicin complex. These disclosures represent the best known prior art. In none of these disclosures is there a teaching, much less a recognition, of the critical features of particle size in the key precipitation step. In the absence of such an awareness, it is readily understood why the prior art disclosures do not even suggest the process of the subject invention.

Unexpectedly, it has been found that a highly desired particle size can be obtained by procedures which contradict prior art teachings. Thus, it has been found that highly concentrated aqueous solutions of an aminoglycoside salt added to an agitated alcohol yields highly desired particles which are easily filtered. This process yields particles that can be filtered as least four times the rate of the filtration of particles obtained by the best known prior art process.

Brief Summary of the Invention

Upon adding a highly concentrated aqueous solution of an aminoglycoside antibiotic salt to a suitable agitated alcohol, there are obtained aminoglycoside antibiotic salt particles which are easily filtered. For example, upon adding an aqueous solution of gentamicin sulfate, having a solids concentration of from about 400 mg./ml. to about 960 mg./ml., to agitated methanol at a ratio of about 4 to about 10 vol. methanol/vol. aqueous, there is obtained the desired particle size precipitate of gentamicin sulfate.

As related above, the solids concentration of the gentamicin concenrate can range from about 400 mg./ml. to about 960 mg./ml. As is readily appreciated by those skilled in the art, the lower level is much higher than disclosed in prior art processes. Further, it should be recognized that the higher range limit is the solubility limit for gentamicin sulfate. Thus, from this result, it can be readily appreciated that other aminoglycoside antibiotics can likewise be used at high concentrations approaching their solubility limit.

Though methanol is exemplified above, it should be clear that any water-miscible lower aliphatic alcohol, for example, ethanol and propanol can also be used.

Aminoglycoside antibiotic salts within the scope of the subject invention include the sulfate, hydrochloride and nitrate salts.

DETAILED DESCRIPTION OF THE INVENTION

The following examples are illustrative of the process of the invention, but are not to be construed as limiting.

EXAMPLE 1

Gentamicin Sulfate

The foregoing aqueous concentrate of gentamicin sulfate can be obtained, for example, by following the procedures disclosed in U.S. Pat. No. 3,091,572, Example 4. The solids concentration of the aqueous gentamicin sulfate solution is varied either by concentration or by dilution with water to give a solids concentration of about 600 mg./ml. This aqueous concentrate is then added to five volumes of agitated methanol per volume of aqueous. The addition is over a period of about 30 minutes at room temperature. The amorphous precipitate of gentamicin sulfate which forms is readily filtered using a standard fritted-disk filter.

EXAMPLE 2

Neomycin Sulfate

The foregoing aqueous concentrate of neomycin can be obtained, for example, by following the procedures disclosed in U.S. Pat. No. 2,799,620. The solids concentration of the aqueous neomycin sulfate solution is varied either by concentration or by dilution with water to give a solids concentration of about 600 mg./ml. This aqueous concentrate is then added to five volumes of agitated methanol per volume of aqueous over a period of 30 minutes at room temperature. The amorphous precipitate of neomycin sulfate which forms is readily filtered using a standard fritted-disk filter.

EXAMPLE 3

Using the procedures of Examples 1 and 2, the solids concentration of the aqueous can be varied from about 400 mg./ml. to the solubility point of the aminoglycoside antibiotic; the alcohol can be substituted by ethanol or propanol; the volume ratio of alcohol can be varied between about 4 to about 10 (alcohol vol./vol. aqueous); and the time of addition can be varied to about 30 minutes to about 4 hours to give readily filterable particles of the desired aminoglycoside antibiotic sulfate.

EXAMPLE 4

By substituting the aminoglycoside antibiotic sisomicin for those in the above examples, there is obtained a precipitate of this antibiotic salt which has desirable particle size for subsequent filtration.

As noted previously, the salt form can be selected from the group of sulfate, hydrochloride and nitrate salts for any of the aminoglycoside antibiotics. Thus, the appropriate acid, hydrochloric and nitric, is used when preparing their respective salts.

We claim:

1. A process for precipitating an amorphous aminoglycoside antibiotic salt, selected from the group consisting of sulfate, hydrochloride and nitrate salt, from an aqueous solution containing the same which comprises:
   (a) concentrating said aqueous solution to a solids concentration of about 400 mg./ml. to the solubility limit of the aminoglycoside antibiotic to obtain an aqueous concentrate; and
   (b) adding said aqueous concentrate to an agitated water-miscible lower aliphatic alcohol at a ratio of about 4 to about 10 vol. alcohol/vol. aqueous to obtain an amorphous precipitate of the aminoglycoside anitibiotic salt.

2. A process, according to claim 1, wherein said aminoglycoside antibiotic salt is gentamicin sulfate.

3. A process, according to claim 1, wherein said aminoglycoside antibiotic salt is neomycin sulfate.

4. A process, according to claim 1, wherein said aminoglycoside antibiotic salt is sisomicin sulfate.

5. A process, according to claim 1, wherein said misible lower aliphatic alcohol is methanol.

6. A process for precipitating amorphous gentamicin sulfate from an aqueous solution containing the same which comprises:
   (a) concentrating said aqueous solution to a solids concentration of about 400 mg./ml. to about 960 mg./ml. to obtain an aqueous concentrate of gentamicin sulfate; and
   (b) adding said aqueous concentrate to an agitated water-miscible lower aliphatic alcohol at a ratio of about 4 to about 10 vol. alcohol/vol. aqueous to obtain an amorphous precipitate of gentamicin sulfate.

7. A process, according to claim 6, wherein said alcohol is methanol.

8. A process, according to claim 7, wherein said methanol is used at a ratio of about 5 volumes/volume of aqueous concentrate.

9. A process, according to claim 6, wherein said solids concentration is about 600 mg./ml., said alcohol is methanol at a ratio of about 5 volumes/volume of aqueous concentrate.

* * * * *